United States Patent [19]

Koppel et al.

[11] Patent Number: 4,552,888
[45] Date of Patent: Nov. 12, 1985

[54] ASCORBIC ACID ETHERS IN ANGIOGENE

[75] Inventors: Gary A. Koppel; Russell L. Barton; Jesse R. Bewley, all of Indianapolis; Stephen L. Briggs, Clayton; Joseph W. Parton, Greenfield, all of Ind.

[73] Assignee: Eli Lilly and Company, Indianapolis, Ind.

[21] Appl. No.: 536,474

[22] Filed: Sep. 28, 1983

Related U.S. Application Data

[63] Continuation-in-part of Ser. No. 339,344, Jan. 15, 1982, abandoned.

[51] Int. Cl.$^4$ ............................................. A61K 31/375
[52] U.S. Cl. .................................... 514/474; 514/414; 514/467; 549/315; 548/465
[58] Field of Search ........................ 549/315; 548/465; 424/280, 274; 514/474, 414, 467

[56] References Cited

U.S. PATENT DOCUMENTS

| | | | |
|---|---|---|---|
| 4,111,958 | 9/1978 | Crawford | 260/340.7 |
| 4,153,613 | 5/1979 | Bharucha et al. | 260/340.9 |
| 4,208,434 | 6/1980 | Iacobucci et al. | 426/72 |

OTHER PUBLICATIONS

Langer, et al., Proc. Nat'l. Acad. Sci., 77, 4331, (1980).
R. Auerbach, Lymphokines, 4, 69, (1981).
Judah Folkman, Ann. Int. Med., 82, 96, (1975).
Research Resources Reporter, Dec. 1981, p. 7.
T. H. Maugh, III, Science, 216, 1304, (1982).
W. N. Haworth, et al., J. Chem. Soc., 1934, 1556.
R. W. Herbert, et al., J. Chem. Soc., 1933, 1270.
T. Reichstein, et al., Helv. Chim. Acta., 17, 510, (1934).
C. S. Vestling and M. C. Rebstock, J. Biol. Chem., 164, 631, (1946).
N. Bezssonoff and R. Sacrez, C. R. Soc. Biol., 124, 356, (1937).
N. Bezssonoff, C. R. Acad., Sci., 180, 970, (1925).
B. S. Gould, et al., Arch. Biochem., 23, 205, (1949).
V. R. Shrihatti, et al., Ind. J. Chem., 15B, 861, (1977).
B. Rokosova and M. Chvapil, Connective Tissue Res., 2, 215, (1974).
T. Radford, et al., J. Org. Chem., 44, 658 (1979).
H. A. Parish, et al., Carbo. Res., 102, 302, (1982).
J. Y. Lew and M. Heidelberger, Carb. Res., 52, 255, (1976).
I. R. Siddiqui and V. L. N. Murty, Carb. Res., 8, 477, (1976).
I. R. Siddiqui, Carb. Res., 9, 344, (1969).
A. G. A. Jackson and J. K. N. Jones, Can. J. Chem., 43, 450, (1965).
M. E. Jung and T. J. Shaw, J.A.C.S., 102, 6304, (1980).
Cancer Biology, Ruddon, Chapter 7, pp. 283–291.
Ciba Foundation Symposium 100–1983-Ryal, et al., Physical Factors and Angiogenesis, pp. 80–89.
Majewski, et al., Int. J. Cancer, 33, 831–833.
National Formulary XIV, (1975), p. lxxviii.

*Primary Examiner*—Jane T. Fan
*Attorney, Agent, or Firm*—James L. Rowe; Arthur R. Whale

[57] ABSTRACT

Ethers of ascorbic and isoascorbic acid and ketals and acetals thereof, angiogenesis inhibitors.

20 Claims, No Drawings

ASCORBIC ACID ETHERS IN ANGIOGENE

CROSS-REFERENCE

This application is a continuation-in-part of our copending application Ser. No. 339,344 filed Jan. 15, 1982 now abandoned.

BACKGROUND OF THE INVENTION

Angiogenesis (or neovascularization), the development of blood vessels, plays an important role in embryonic development, in the inflammatory response, in the development of metastases (tumor induced angiogenesis or TIA), in diabetic retinopathy, in the formation of the arthritic panus and possibly in psoriasis. In tumor angiogenesis, for example, capillary sprouts are formed, their formation being induced by a group of tumor cells. These sprouts eventually develop into a microcirculatory network within the tumor mass. There are two principle types of tumor angiogenesis in terms of the events which follow implantations of metastatic seedlings on surfaces and in organs.

The first or primary angiogenesis is the initial vascularization of the mass of multiplying tumor cells and is regarded as an essential prerequisite for the survival and further growth of a metastatic deposit.

The second is a continuing or secondary angiogenesis and is the phenomenon which occurs in waves at the periphery of a growing tumor mass. This second angiogenesis is essential for the accretion of new microcirculatory territories into the service of the expanding and infiltrating tumor.

Auerbach, *Lymphokines*, 4, 69 (1981) reviews angiogenesis inducing factors. Judah Folkman, one of the pioneers in this field reviews tumor angiogenesis in *Ann. Int. Med*, 82 96 (1975) and discussed evidence for the existence of a diffusible tumor angiogenesis factor (TAF).

Several naturally-occurring angiogenesis inhibitors have been found. *Research Resources Reporter*, page 7, December, 1981 reports the isolation of a factor from cartilege which slows tumor growth and also reports similar factors from other tissues. These factors (AI) all seems to be proteins of 3,500 to 25,000 daltons. Other diseases to be treated with AI include arthritis, diabetic or sickle-cell retinopathy and psoriasis. *Science* 216, 1304 (1982) reported the characterization of a specific AI protamine by Folkman and Taylor [(see also *Nature*, 297, 307(1982)] which factor inhibited lung metastases and B16 melanoma in mice. Simple, small molecular weight chemical AI's were not known as of Jan. 1, 1982.

Methyl ethers of ascorbic acid were synthesized by Haworth and coworkers during the classical elucidation of the structure of ascorbic acid-vitamin C. The 3-methyl, 2,3-dimethyl and 2,3,5,6-tetramethyl ethers are described (see *J. Chem. Soc.*, 1934, 1556). Diazomethane was used as the methylating agent. Herbert et al. *J. Chem. Soc.*, 1933 1270 also prepared the mono, di and tetramethyl ethers of ascorbic acid, using dimethyl sulfate and base (50% aqueous KOH) for the monoether, diazomethane for the diether and silver oxide plus MeI for the tetramethyl ether from the dimethyl ether.

Reichstein et al., *Helv. Chim. Acta*, 17, 510 (1934) also prepared the 3-methyl ether of ascorbic acid using diazomethane, and then prepared a ketal therefrom with acetone.

Vestling and Rebstock, *J. Biol. Chem*, 164, 631 (1946) investigated the antiscorbutic activity of 3-methylascorbic acid (prepared via diazomethane) by intraperitoneal injection of an ascorbic acid solution in distilled water into scorbutic guinea pigs. Bezssonoff and Sacrez, C. R. *Soc. Biol*, 124, 356 (1937) earlier had found that 2,3-dimethylascorbic acid was devoid of Vitamin C activity but that the 3-methyl ether was active. The compounds were administered orally in aqueous solution. Gould et al., *Arch. Biochem.*, 23, 205 (1949) verified the fact that 3-methylascorbic acid had about 1/50 the vitamin C activity of ascorbic acid. For test purposes, the compound was added to the diet of scorbutic guinea pigs. Shrihatti et al, *Indian J. Chem.*, 15B, 861 (1977) attempted to resolve the divergent reports on the vitamin C activity of the 3-methyl ether of ascorbic acid and developed an unambiguous procedure for preparing that compound and also the 2,3-dimethyl ether. Diazomethane was the methylating agent.

Rokosova and Chvapil, *Connective Tissue* Res., 2, 215 (1974) tested 3-methyl-L-ascorbic acid for its ability to stimulate proline hydroxylation in scorbutic granulomas. The compound had an effect in vitro but was not tested in vivo.

Radford et al *J. Org. Chem.*, 44, 658 (1979) published a carbon-13 nmr of 3-methylascorbic acid, among other compounds, and confirmed the previously assigned structure.

Parish and Gilliom, *Carbo. Res.*, 102, 302 (1982) prepared 3-O-(3,3-dimethyl-2-oxobutyl)ascorbate, (3-t-butyloxymethyl-L-ascorbic acid).

U.S. Pat. No. 4,111,958 prepared ascorbic acid from gulono-14-lactone, galactano-1,4-lactone, iodono-1,4-ketone or talono-14-lactone by protecting, C-2 or C-3 position of the sugar lactone, as by ether formation, and oxidizing the remaining C-2 or C-3 free hydroxyl to yield an ether of ascorbic acid (L or D). The usual ether protecting group was a 3,5 ketal. The oxidized product is thus a 3,5-ketal of ascorbic acid.

Other methylated hexose lactones have been prepared:

2,3,6-tri-O-methyl-D-galactano-1,4-lactone—Lew and Heidelberger, Carb. Res, 52, 255 (1976)

2,3,5-tri, 2,3,5,6-tetra and 3,5-di-O-methyl-D-mannofuranose, Siddiqui and Murty Carb. Res, 8, 477 (1968)

3,5,6-tri-O-methyl-D-mannono-1,4-lactone—Saddiqui, Carb. Res, 9, 344 (1969).

The 3-benzylether of ascorbic acid is reported by Jackson and Jones in *Can. J. Chem.* 43, 450 (1965) as well as the 2,3-dibenzylether and the corresponding-5,6-O-isopropylidene derivatives.

U.S. Pat. No. 4,153,613 discloses the 5,6-O-dodecanal, hexadecanal, tetradecanal and octadecanal acetals of L-ascorbic acid as well as shorter chain acetals. Ketals are also described. The compounds are used to prevent nitrosamine formation in bacon.

Jung and Shaw, *J. Am. Chem. Soc.*, 102, 6304 (1980) utilized the 5,6-acetonide of ascorbic acid or the 2,3-dimethylether of ascorbic acid as a chiral starting material for preparing (R)-glycerolacetonide. Diazomethane was used to prepare the dimethyl ether.

U.S. Pat. No. 4,208,434 discloses the use of C-2 and-/or C-3 $C_{1-10}$ alkyl ethers of ascorbic acid and 5,6-ketals thereof, as stabilizers of certain natural anthocyanin pigments to be added to soft drinks.

To summarize, lower alkyl ethers of ascorbic acid and its ketals are known as is the benzyl ether.

SUMMARY

The only published inhibitors of angiogeneric have been fractions derived from natural products.

The methyl ether of ascorbic acid which has been tested for antiscorbutic activity was administrered as an aqueous solution. Ascorbic acid ethers have not been the active drug in pharmaceutical formulations such as capsules, tablets, emulsions etc.

OBJECTS OF THE INVENTION

It is apparent that a chemical which would inhibit angiogenesis, either by competitively inhibiting an angiogenesis factor or by some other mechanism, would have an adverse effect upon the growth of tumors, on the development of retinopathy or rheumatoid arthritis, or on the development of the psoriatic lesion. It is an object of this invention to provide a group of compounds which inhibit angiogenesis wherever found, to provide novel formulations for these angiogenesis inhibitors when used as drugs and to provide novel angiogenesis inhibitors of high potency.

SUMMARY OF THE INVENTION

In fulfillment of the above and other objects, this invention provides a method of inhibiting angiogenesis which comprises administering to a mammal in need of treatment an angiogenesis inhibiting dose of a compound of the formula

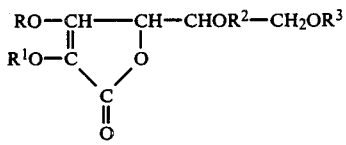

wherein R and $R^1$ are individually H or $CH_2R^4$, except that at least one of R and $R_1$ must be other than H, wherein $R^4$ is H, $(C_1-C_{21})$alkyl-$R^5$, $(C_2-C_{12})$alkenyl, $(C_2-C_{12})$alkynyl, $(C_3-C_8)$cycloalkyl, $(C_3-C_8)$cycloalkenyl, $(C_7-C_{12})$bicycloalkyl or $(CH_2)_m$ Z, wherein $R^5$ is CN, OH, H, O-$(C_1-C_5)$ alkyl, O-$(C_2-C_4)$ haloalkyl, phthalimido, $COOR^8$, OZ or $N(CH_3)_2$; m is 0, 1 or 2 and Z is

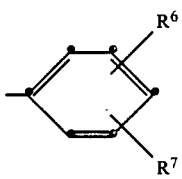

wherein $R^6$ and $R^7$ are individually halo, $CF_3$, H, $(C_1-C_3)$alkyl, O-$(C_1-C_3)$alkyl or $NO_2$ and $R^8$ is H or $(C_1-C_3)$alkyl, except that when $R^4$ is $(C_1-C_{21})$alkyl-$R^5$ and $R^5$ is O-$(C_1-C_5)$alkyl, O-$(C_2-C_4)$haloalkyl or OZ, the total number of carbon atoms in $R^4$ is less than 22;

$R^2$ and $R^3$, when taken singly are H, $(C_1-C_{12})$alkyl or $C_2$-phenyl;

$R^2$ and $R^3$, when taken together, are

wherein $R^9$ is $(C_1-C_{10})$alkyl, [(preferably $(C_1-C_5)$alkyl)], halo-substituted $(C_1-C_{10})$alkyl, Z, or $(C_1-C_{10})$alkyl-Z and $R^{10}$ is a same or different $R^9$ or H.

The above formula represents ethers of ascorbic or isoascorbic acid or of 5,6-ketals thereof. Ascorbic acid and isoascorbic can be represented by the formula

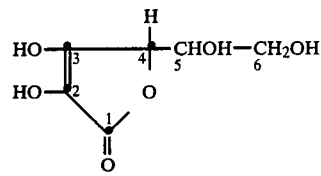

In formula II, $C_4$ and $C_5$ are asymmetric carbons; thus, formula II represents 4 stereoisomers of 3-ketohexuronic acid lactone (enol form). The absolute stereochemical configuration of these 4 stereoisomers and the corresponding trivial names are as follows.

$C_4(R)C_5(S)$ 3-ketohexuronic acid lactone (enol form), known as L-ascorbic acid $C_4(R)C_5(R)$ 3-ketohexuronic acid lactone (enol form), known as D-isoascorbic acid $C_4(S)C_5(R)$ 3-ketohexuronic acid lactone (enol form), known as D-ascorbic acid $C_4(S)C_5(S)$ 3-ketohexuronic acid lactone (enol form), known as L-isoascorbic acid L-ascorbic acid (vitamin C) can also be named as 3-oxo-L-gulofuranolactone (enol form) and it is a derivative of L-gulofuranose. Likewise, D-ascorbic acid is a derivative of D-gulofuranose. The isoascorbic acids are derivatives of D- and L-glucofuranose. Compounds according to the above formula can be named systematically as derivatives of 2-oxo-3,4-dihydroxy-5-(1,2-dihydroxyethyl)-2,5-dihydrofuran; ie. L-ascorbic acid would be $C_4(R)C_5(S)$ 2-oxo-3,4-dihydroxy-5-(1,2-dihydroxyethyl)-2,5-dihydrofuran. However, the hexuronic acid terminology is preferred and will be used throughout in referring to compounds according to formula II.

The terms "ascorbic acid" and "isoascorbic acid" as used herein includes all 4 stereoisomers unless a given absolute configuration is specified.

It will be recognized that when $R^2$ and $R^3$ are taken together to form

and $R^{10}$ is other than H the resulting structure is a ketal and, when $R^{10}$ is H, an acetal. For example, if $R^9$ is methyl and $R^{10}$ is ethyl, the resulting compound is a ketal of methyl ethylketone formed with the vicinal hydroxyls at C-5 and C-6. A preferred group of compounds are those in which R and/or $R^1$ is a $C_{14}-C_{22}$ straight chain alkyl ($CH_2R^4$ where $R^4$ is $C_{13}-L_{21}$ straight chain alkyl).

In the above formulas, the following aliphatic radicals exemplify the terms R, $R^1$, $R^2$, $R^3$, $R^4$, $R^8$, $R^9$ and $R^{10}$.

Ethyl, n-propyl, isopropyl, sec.-butyl, n-butyl, isobutyl, iso-amyl, t-amyl, n-amyl, 2-pentyl, 3-pentyl, 3-methyl-2-butyl, 2-hexyl, 1-hexyl, 3-hexyl, 4-methyl-1-pentyl, 3-methyl-1-pentyl, 3-methyl-2-pentyl, neopentyl, 3,3-dimethyl-1-butyl, 3,3-dimethyl-1-pentyl, 3,3,4-trimethyl-1-pentyl, 2,2,4-trimethyl-1-pentyl, 2,4,4-dimethyl-2-pentyl, iso-octyl, isoheptyl, n-heptyl, 2-heptyl, 3-heptyl, 4-heptyl, 2-octyl, 3-octyl, 4-octyl, 2-methyl-2-butenyl, 2-methyl-3-propenyl, allyl, methallyl, crotyl, cyclobutyl, cyclopropyl, cyclopentyl, cyclohexyl, 3-methylcyclopentyl, 3-ethylcyclohexyl, cycloheptyl, 4-methylcycloheptyl, 2-methylcycloheptyl, cyclooctyl, 1-cyclohexenyl, 2-cyclohexenyl, 3-cyclohexenyl, 2-cyclopentenyl, 3-ethyl-2-cyclohexenyl, 2-cyclopentenyl, 4-methyl-2-cycloheptenyl, 4-cyclooctenyl, 2-bromoethyl, 2-iodoethyl, benzyl, o-chlorobenzyl, m-bromobenzyl, 2,4-dichlorobenzyl, p-nitrobenzyl, 2-iodobenzyl, 4-fluorobenzyl, 1methyl-4-trifluoromethylbenzyl, 2-methyl-2-chlorobenzyl, m-ethoxybenzyl, bicyclo[2.2.1]heptanyl, bicyclo[2.2.1]heptanylmethyl, bicyclo[2.2.1]heptenyl, bicyclo[2.2.1]heptenylmethyl, bicyclo[3.3.0]octanyl, bicyclo[2.4.0]octenyl, bicyclo[3.3.0]octenylethyl, bicyclo[3.3.1]nonyl, bicyclo[3.3.1]nonylmethyl, bicyclo[3.3.1]nonenyl, bicyclo[3.3.1]nonenylmethyl, bicyclo[3.1.1]heptanyl, bicyclo[3.3.1]heptanylpropyl, bicyclo[3.1.1]heptenyl, bicyclo[3.1.1]heptenylmethyl, bicyclo[4.2.0]octanyl, bicyclo[4.2.0]octenyl, bicyclo[4.2.0]octenylmethyl, 3-methylbicyclo[4.2.0]octenyl, bicyclo[4.3.1]cyclododecyl, bicyclo[4.3.1]cyclodecylmethyl, bicyclo[5.3.0]cyclodecenyl, 5-methylbicyclo[5.3.0]cyclododecenyl, bicyclo[3.2.0]heptanyl, bicyclo[3.2.0]heptanylethyl, bicyclo[3.2.0]heptenyl, bicyclo[3.2.0]heptenylmethyl, bicyclo[4.1.0]heptanyl, bicyclo[4.1.0]heptanylmethyl, bicyclo[4.1.0]heptenyl, bicyclo[4.1.0]heptenylmethyl, 2-isopropylbicyclo[4.1.0]heptenyl, 2-isopropyl-3-methylbicyclo[3.1.0]hexenyl, n-hendecyl, n-dodecyl, n-tridecyl, n-tetradecyl, n-pentadecyl, n-hexadecyl, n-heptadecyl, n-octadecyl, n-eicosyl, n-docosyl, 2-tetradecyl, 4-tetradecyl, 6-tetradecyl, 7-tetradecyl, 7-hexadecyl, 8-hexadecyl, 9-octadecyl, 2-octyldodecyl, 3,7,11-trimethyldodecyl, tetrahydrogeranyl, 12-methyltridecyl, myristoleyl, myristeladyl, oleyl, linoleyl, 12-methyltridecen-9-yl etc.

The compounds of this invention can be prepared by reacting ascorbic acid, or isoascorbic acid or a ketal or acetal thereof (III) (wherein $R^2$ and $R^3$ have their previously assigned meanings)

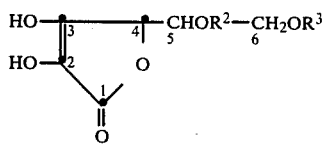
III with one or two moles of a base such as an alkali metal lower alkanolate plus one or two moles of an alkylating agent, RX, wherein X is a leaving group (a group labile to nucleophilic displacement) such as halogen, (Cl, I, Br) or is a halogen-like leaving group; i.e., p-tosyl (p-toluene sulfonate) or mesyl (methane sulfonate). A dialkyl sulfate ($R_2SO_4$) can also be used. If one mole each of base and RX is used, the above reaction produces an ether group at C-3. If it is desired to prepare a diether, with identical ether groups at both C-2 and C-3, two moles of the base and two moles of RX are used. The resulting compound is a diether according to I in which R and $R^1$ represent the same group. If a diether is desired in which R and $R^1$ are different groups, a monoether according to I in which R is ethyl, for example, and $R^1$ is H is reacted with an alkylating reagent $R^1X$ and one mole of base, $R^1$ being other than ethyl; e.g., methyl.

Depending on the relative reactivities of the C-2 and C-3 hydroxyl groups and of the alkylating agent, RX, a certain amount of reaction takes place at C-2 even if only one mole of alkylating agent is used. The mixture of mono and diethers thus formed can be readily separated, as by chromatography. There is also a possibility, where $R^2$ and $R^3$ are hydroxyls, of partially alkylating one of these and forming a diether at C-3 and C-5, for example. Such diethers can also be separated by chromatography.

The above etherification reactions are carried out in a mutual inert solvent, customarily at ambient temperature. DMSO (dimethylsulfoxide) is preferred as a solvent. The preferred base is sodium methylate.

Under certain circumstances, particularly where there is a competing reaction with the C-5 or C-6 hydroxy, the L-ascorbic acid ethers can be prepared in exceptionally pure form by alkylating L-ascorbic acid 5,6-acetonide (I where $R^2$ and $R^3$ together form a 1-methylethylidine group —

—wherein both $R^9$ and $R^{10}$ are methyl) and then removing the acetonide ketal group by treatment with acid—acetic, 1% HCl etc. This procedure selectively hydrolyzes the ketal group without affecting the ether groups at C-2 and/or C-3.

The ketal and acetal starting materials (I when $R^2$ and $R^3$ together form

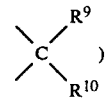
)

are prepared by standard procedures such as a reaction with the desired ketone or aldehyde in dioxane or other mutual inert anhydrous solvent in the presence of an excess of a Lewis acid; e.g., zinc chloride or the like.

This invention is further illustrated by the following specific examples:

EXAMPLE 1

Preparation of 3-O-n-Butyl-L-ascorbic acid

A reaction mixture was prepared containing the following ingredients: 33 g. of L-ascorbic acid, 10.2 g. of sodium methylate, 34.5 g. of n-butyl iodide and 250 ml. of DMSO. The reaction mixture was stirred at ambient temperature and the progress of the reaction monitored by thin layer chromatography. After 24 hours, the reaction mixture was added to 500 ml. of ethyl acetate. 3-O-n-Butyl-L-ascorbic acid formed in the above reaction precipitated and was separated by filtration. Further precipitation was caused by adding 300 ml. of toluene to the filtrate. These crystals were also collected and the combined crystals dissolved in 500 ml. of methanol. (weight=about 20 g.) 45 g. of silica gel was added to this solution. The solution was evaporated to dryness in vacuo.

A chromatographic column was prepared in the following manner: 100 g. of silica 60 were mixed with 500 ml. of hexane. This mixture was placed in a glass chromatographic column containing a glass wool plug covered by a 3–5 mm. layer of sea sand under a nitrogen atmosphere. The silica gel was allowed to compact for a period of about 20 minutes. Another 2–4 mm. layer of sea sand was added. It was necessary in both instances that the sea sand layers be leveled. Next the silica-precipitate dried mixture was mixed with hexane and this mixture added carefully to the top of the column. Next, about a 5 g. quantity of silica in hexane was added. The column was again placed under nitrogen atmosphere for 15–20 minutes while the two new silica layers were compacting. Finally, a layer of sand (3–6 mm. thick) was added.

The chromatogram was developed as follows: 8 l. of a 1:1 ethyl acetate/toluene mixture were passed through the column. No substantial amounts of the desired L-ascorbic acid ether were obtained. Next, 4 l. of a 3:1 ethyl acetate/toluene eluate were passed through the column, thereby eluting most of the desired ether. Evaporation of the solvent yielded 3-O-n-butyl-L-ascorbic acid having the following analysis:

Calculated: C, 51.72; H, 6.94; Found: C, 51.45; H, 6.72.

Mass spectrum: peaks at 232 (molecular ion), 172, 145, 100, 85, 71, 57, 41, 29.

Other compounds prepared by the above procedure include:

3-O-(2,6-dichlorobenzyl)-L-ascorbic acid.
Analysis calculated: C, 46.59; H, 3.61; Cl, 21.16; Found: C, 46.34; H, 3.53; Cl, 20.88.
Mass spectrum: peaks at 428 (molecular ion), 192.

3-O-allyl-L-ascorbic acid
Mass spectrum: peaks at 216 (molecular ion) 156, 58, 40.

2,3di-(O-allyl)-L-ascorbic acid
Analysis calculated: C, 56.25; H, 6.29; Found: C, 56.12; H, 5.93.
Mass spectrum: peaks at 256 (molecular ion) 216, 174, 58, 40.

3-O-n-dodecyl-L-ascorbic acid
Yield=7.183 g. from 33.0 g. of L-ascorbic acid
Mass spectrum: peaks at 344 (molecular ion) 284, 177, 145, 116, 100, 85, 71, 61, 57, 43, and 29.

3-O-(3-bromobenzyl)-L-ascorbic acid
Yield=3.986 g. from 17.6 g. of L-ascorbic acid
Analysis calculated: C, 45.24; H, 3.80; Br, 23.15; Found: C, 45.45; H, 3.57; Br, 22.94.
pKa=10.50

3-O-(3-fluorobenzyl)-L-ascorbic acid
Yield=4.194 g. from 23.3 g. of L-ascorbic acid
Analysis calculated: C, 54.93; H, 4.61; F, 6.68; Found: C, 55.07; H, 4.42; F, 6.49.
Mass spectrum: molecular ion at 284

3-O-(ω-hydroxycarbonyldecyl)-L-ascorbic acid
Analysis calculated: C, 56.66; H, 7.83; Found: C, 56.93; H, 7.55.
Mass spectrum: peaks at 361 (molecular ion), 58.

3-O-n-pentadecyl-L-ascorbic acid
Yield=3.6 g. from 15.2 g. of L-ascorbic acid
2,3-di-(O-n-pentadecyl)-L-ascorbic acid (isolated from the same reaction mixture as the monoether)
Analysis calculated: C, 72.49; H, 11.48; Found: C, 72.64; H, 11.28.
Yield=1.26 g.

3-O-(2-bromoethoxyethyl)-L-ascorbic acid
Analysis calculated: C, 36.72; H, 4.62; Br, 24.43; Found: C, 36.46; H, 4.92; Br, 24.23.

Mass spectrum: peaks at 328, 326, 382, 58

3-O-(3-phenoxypropyl)-L-ascorbic acid
Analysis calculated: C, 58.06; H, 5.85; Found: C, 58.17; H, 5.59.
Mass spectrum: peaks at 310 (molecular ion).

3-O-(2-phthalimidoethyl)-L-ascorbic acid
Mass spectrum: peaks at 349 (molecular ion) 193, 174, 161, 148, 130, 102, 76, 44, 28.

3-O-n-hexadecyl)-L-ascorbic acid
Analysis calculated: C, 65.97; H, 10.07; O, 23.97; Found: C, 66.24; H, 9.84; O, 24.07.
Titration: pKa=11.10.
Infrared spectrum: $\nu$ at 1750, 1695, 1680 cm$^{-1}$ 2,3-di-(O-n-hexadecyl)-L-ascorbic acid
Analysis calculated: C, 73.03; H, 11.61; O, 15.36; Found: C, 72.92; H, 11.88; O, 15.07.
Infrared spectrum: $\nu$ at 1740, 1680 cm$^{-1}$
Titration-no titratable group 3-O-n-heptadecyl-L-ascorbic acid
Analysis calculated: C, 66.63; H, 10.21; Found: C, 66.37; H, 9.93.
Infrared spectrum: $\nu$ at 1760, 1710, 1695 cm$^{-1}$
Mass spectrum: peaks at 414 (molecular ion) 354, 177, 116, 97

3-O-m-octadeyl-L-ascorbic acid
Analysis calculated: C, 67.26; H, 10.35; Found: C, 67.42; H, 10.37.
Infrared spectrum; $\nu$ at 1757, 1705, 1690 cm$^{-1}$
Mass spectrum: peaks at 428 (molecular ion), 297, 98, 63

2,3-di-(-O-n-octadecyl)-L-ascorbic acid
Analysis calculated: C, 74.07; H, 11.84; Found: C, 74.34; H, 12.07.
Infrared spectrum: $\nu$ at 1770, 1680 cm$^{-1}$ 3-O-benzyl-L-ascorbic acid
Analysis calculated: C, 58.65; H, 5.30; Found: C, 58.53; H, 5.60;
Mass spectrum: peaks at 266 (molecular ion), 228, 166, 148, 107, 91
Infrared spectrum: $\nu$ at 1760, 1695 cm$^{-1}$ 3-O-(3-chlorobenzyl)-L-ascorbic acid
Analysis calculated: C, 51.93; H, 4.36; Cl, 11.79 Found: C, 51.77; H, 4.10; Cl, 12.09.
Infrared spectrum: $\nu$ at 1740, 1690, 1680 cm$^{-1}$
Mass spectrum: peaks at 300 (molecular ion) 240, 147, 125, 89

3-O-(4-chlorobenzyl)-L-ascorbic acid
Analysis calculated: C, 51.93; H, 4.36; Cl, 11.79; Found: C, 51.71; H, 4.21; Cl, 11.86.
Infrared spectrum: $\nu$ at 1755, 1695 cm$^{-1}$
$^{13}$C nmr: $\delta$ at 170.36, 150.09, 135.62, 132.82, 129.53, 129.42, 119.73, 74.63, 71.06, 68.58, 61.82.

3-O-(3-trifluoromethylbenzyl)-L-ascorbic acid
Analysis calculated: C, 50.31; H, 3.92; F, 17.05; Found: C, 50.59; H, 3.40; F, 17.00.
Infrared spectrum: $\nu$ at 1755, 1695 cm$^{-1}$
Mass spectrum: peaks at 334 (molecular ion), 295, 274, 228, 199.
$^{13}$C nmr: $\delta$ at 170.32, 149.94, 119.85, 74.66, 71.14, 68.62, 61.81.

3-O-(3-methylbenzyl)-L-ascorbic acid
Analysis calculated: C, 60.00; H, 5.75; Found: C, 60.21; H, 5.82.
Infrared spectrum: $\nu$ at 1740, 1685, 1675 cm$^{-1}$
Mass spectrum: peaks at 280 (molecular ion) 262, 186, 162, 134, 105, 91.

3-O-(2,5-dimethylbenzyl)-L-ascorbic acid
Analysis calculated: C, 61.22; H, 6.17; Found: C, 61.02; H, 6.22.
Infrared spectrum: $\nu$ at 1755, 1695 cm$^{-1}$ Mass spectrum: peaks at 294 (molecular ion), 176, 158, 147, 131, 119, 91.

3-O-n-octadecyl-D-ascorbic acid

Analysis calculated: C, 67.3; H, 10.4; Found: C, 67.1; H, 10.4.

Infrared spectrum: $\nu$ at 1700, 1755, 2840, 2905 cm$^{-1}$

Mass spectrum: molecular ion at 428

Titration: pKa=11.00.

3-O-n-octadecyl isoascorbic acid

Analysis calculated: C, 67.3; H, 10.4; Found: C, 66.8; H, 9.3.

Titration: pKa=11.60.

Mass spectrum: molecular ion at 428

Infrared spectrum: $\nu$ at 1695, 1755, 2840, 2905 cm$^{-1}$

3-O-(2-methylbenzyl)-L-ascorbic acid

Analysis calculated: C, 60.00; H, 5.8; O, 34.2; Found: C, 59.9; H, 5.5; O, 34.1.

Titration: pKa=10.78.

Mass spectrum: E+ =280

Infrared spectrum: $\nu$ at 1685, 1750, 3370 cm$^{-1}$

2-O-(3-dimethylaminopropyl)-3-O-n-octadecyl-L-ascorbic acid hydrochloride

Analysis calculated: C, 63.31; H, 10.26; N, 2.55; Cl, 6.44; Found: C, 63.10; H, 10.13; N, 2.69; Cl, 6.66.

Infrared spectrum: $\nu$ at 1762, 1675 cm$^{-1}$

Titration: pKa=8.0

Mass spectrum: peaks at 513, 482, 415, 344, 260, 201, 160.

EXAMPLE 2

Preparation of 3-O-n-butyl-5,6-O-(benzylidene)-L-ascorbic acid

Following the procedure of Example 1, a reaction mixture was prepared from 150 ml. of DMSO, 15 g. of 5,6-O-benzylidene-L-ascorbic acid, 3.24 mg. of sodiumm methylate and 10.5 g. of n-butyl iodide. The reaction mixture was stirred at ambient temperature for about 72 hours at which time TLC indicated that the reaction had gone substantially to completion. The reaction mixture was extracted with 600 ml. of ethyl acetate and the ethyl acetate extract itself extracted with 300 ml. portions of saturated aqueous sodium chloride. The ethyl acetate extract was dried, decolorized with charcoal, filtered and the solvent removed from the filtrate in vacuo. A residue weighing about 15 g. was obtained. Preparative TLC over silica indicated three bands (using a 1:2:2 methanol/toluene/ethyl acetate solvent system). Bands containing the desired n-butylether were scraped from the preparative plates, extracted with the same solvent system and rechromatographed using a 1:2 ethyl acetate/toluene solvent system. A final yield of 5.54 g. of 3-O-n-butyl-5,6-benzylidene-L-ascorbic acid was obtained.

Mass spectrum: peaks at 320 (molecular ion) 247, 223, 179, 149, 107, 91, 77, 56, 52, 43, 29 and 15.

The following additional compound was obtained by the above procedure:

3-(2-methoxyethyl)-5,6-O-benzylidine-L-ascorbic acid

Analysis calculated: C, 59.62; H, 5.63; Found: C, 59.33; H, 5.49.

Mass spectrum: peaks at 149, 91, 77, 59, 44, 30; minor peaks at 322 (M+) 281, 247, 223, 174 and 18.

EXAMPLE 3

Alternate preparation of 3-O-n-Butyl-L-ascorbic acid

About 0.5 g. of 3-O-n-butyl-5,6-O-benzylidene-L-ascorbic acid from Example 2 were dissolved in 20.0 ml. of glacial acetic acid. Five ml. of water were then added and the subsequent reaction mixture stirred at ambient temperature. After about 1.5 hours, TLC indicated that about 50–60% of the starting material still remained; the reaction mixture was therefore allowed to stir at ambient temperature for an additional 48 hours. TLC then indicated that the conversion of the benzylidine derivative to 3-O-n-butyl-L-ascorbic acid was substantially complete. The product was purified by preparative thin layer chromatography over silica using a 1:2:1 methanol/toluene/ethyl acetate eluant. Chemical analysis and other physicochemical measurements indicated that the product of Example 1 had been obtained in pure form.

EXAMPLE 4

Preparation of 5,6-O-benzylidene-L-ascorbic acid

Ascorbic acid (89.2 g.) was slurried in 400 ml. of p-dioxane, 200 g. of zinc chloride were added slowly and the resulting mixture was stirred for one hour. Next, 100 ml. (104 g.) of benzaldehyde were added. This reaction mixture was stirred at ambient temperature for about 24 hours and was then extracted with 500 ml. of ethyl acetate. The ethyl acetate extract was itself extracted with three portions of saturated aqueous sodium chloride. The ethyl acetate solution was dried and the dried solution treated with activated charcoal and then filtered through cellulose. Concentration of the filtrate caused 5,6-O-benzylidene-L-ascorbic acid to crystallize.

Analysis calculated: C, 59.09; H, 4.58; Found: C, 59.19; H, 4.34.

Yield=18.3 g.

Other acetals prepared by the above procedure include 5,6-O-(2-phenylethylidene)-L-ascorbic acid Analysis calculated: C, 60.4; H, 5.1; Found: C, 60.3; H, 5.2.

Infrared spectrum: $\nu$ at 3258, 1755, 1664 cm$^{-1}$

Mass spectrum: M+ =278

5,6-O-undecylidene-L-ascorbic acid

Infrared spectrum; $\nu$ at 1665, 1750, 2840, 2920 cm$^{-1}$

Titration: pKa=6.48

Mass spectrum: M+ =327

EXAMPLE 5

Preparation of 5,6-O-(1-methylethylidene)-L-ascorbic acid

A reaction mixture was prepared from 88 g. of L-ascorbic acid, 400 ml. of dioxane, 200 g. of zinc chloride and 750 ml. of acetone. The reaction mixture was stirred at ambient temperature overnight, and then was washed over a silica gel 60 column using a toluene-methanol (1:1) solution as the eluant. 600 ml. of wash were collected and the solvent removed therefrom in vacuo. Acetone was added and the solid product filtered. The collected crystals were washed with toluene. A yield of 35.6 g. of 5,6-O-(1-methylethylidene)-L-ascorbic acid was recovered. The compound had the following physical characteristics:

Infrared spectrum: $\nu$ at 1670, 1760, 3000, 3250 cm$^{-1}$.

Titration: pKa=6.10

Mass spectrum: peaks at 216 (M+), 201.

Following the above procedure, these ketals were prepared.

5,6-O-(1-chloromethylethylidene)-L-ascorbic acid

Analysis calculated: C, 43.1; H, 4.4; O, 38.3; Cl, 14.2; Found: C, 43.4; H, 4.5; O, 38.2; Cl, 13.9.
Titration: pKa=6.10
Mass spectrum: peaks at 250 (M+), 201
Infrared spectrum: $\nu$ at 1675, 1775, 3000, 3300 cm$^{-1}$ 5,6-O-(1-benzyl-2-phenylethylidene)-L-ascorbic acid
Analysis calculated: C, 68.5; H, 5.4; Found: C, 68.2; H, 5.6.
Infrared spectrum: $\nu$ at 1660, 1740 cm$^{-1}$
Titration: pKa=6.55.
Mass spectrum: peaks at 360, 354, 277

EXAMPLE 6

Preparation of 3-O-n-octadecyl-5,6-O-(1-methylethylidene)-L-ascorbic acid

A reaction mixture was prepared from 20 g. of 5,6-O-(1-methylethylidine)-L-ascorbic acid, 5 g. of sodium methylate, 30.9 g. of n-octadecylbromide and 400 ml. of DMSO. The reaction mixture was stirred at ambient temperature for about five days. Water and ethyl acetate were then added and the ethyl acetate layer separated. The desired 3-O-n-octadecyl ether contained in that layer was purified by the procedure of Example 1. Chromatography yielded about 1.62 g. of purified 3-O-n-octadecyl-5,6-O-(1-methylethylidene)-L-ascorbic acid.

Analysis calculated: C, 69.2; H, 10.3; Found: C, 69.2; H, 10.6.
Infrared spectrum: $\nu$ at 1705, 1760, 2870, 2930 cm$^{-1}$
Titration: pKa=11.4
Mass spectrum: peaks at 468, 453

Other ketals preparable by the above procedure include:

3-O-(2,5-dimethoxyphenacyl)-5,6-O-(1-methylethylidene)-L-ascorbic acid
Titration: pKa=10.59
Infrared spectrum: $\nu$ at 1700, 1750, 3340 cm$^{-1}$
Mass spectrum: peaks at 394, 379.

3-O-(2-phthalimidoethyl)-5,6-O-(1-methylethylidene)-L-ascorbic acid
Titration: pKa=10.32
Mass spectrum: peaks at 389, 374.
Infrared spectrum: $\nu$ at 1710, 1780, 3220 cm$^{-1}$ 3-O-(methoxycarbonylmethyl)-5,6-O-(1-methylethylidene)-L-ascorbic acid
Infrared spectrum: $\nu$ at 1700, 1760, 3000, 3340 cm$^{-1}$
Titration: pKa=9.80
Mass spectrum: peaks at 302, 287

3-O-(2-methoxyethyl)-5,6-O-(1-methylethylidene)-L-ascorbic acid
Titration: pKa=10.31
Mass spectrum: peaks at 288, 273
Infrared spectrum: $\nu$ at 1695, 1765, 2990 cm$^{-1}$ 3-O-(2-bromoethoxyethyl)-5,6-O-(1-methylethylidene)-L-ascorbic acid
Analysis calculated: C, 42.5; H, 5.2; Found: C,42.7; H, 5.4.
Titration: pKa—10.4
Infrared spectrum: $\nu$ at 1700, 1770, 3010, 3300 cm$^{-1}$ 2,3-O-bis(n-octadecy-5,6-O-(1-methylethylidene)-L-ascorbic acid
No titratable group
Mass spectrum: 7210 (M+)

2,3-O-bis(4-cyanobutyl)-5,6-O-(1-methylethylidene)-L-ascorbic acid
No titratable group
Infrared spectrum: $\nu$ at 1690, 1750, 2260, 3000 cm$^{-1}$
Mass spectrum: peaks at 378, 363

2,3-O-bis(4-fluorobenzyl)-5,6-O-(1-methylethylidene)-L-ascorbic acid
Infrared spectrum: $\nu$ at 1690, 1765, 2905, 2940, 3005, 3065 cm$^{-1}$
No titratable group.
Mass spectrum: peaks at 432, 214

3-O-(4-nitrobenzyl)-5,6-O-(1-methylethylidene)-L-ascorbic acid
Titration: pKa=10.10
Mass spectrum: peaks at 351, 336
Infrared spectrum: $\nu$ at 1700, 1770, 3360, 3420 cm$^{-1}$ 3-O-(3-phenoxypropyl)-5,6-O-(1-methylethylidene)-L-ascorbic acid
Analysis calculated: C, 61.7; H, 6.3; Found: C, 59.9; H, 5.7.
Infrared spectrum: $\nu$ at 1700, 1780, 3880, 34200 cm$^{-1}$
Titration: pKa=10.7
Mass spectrum: peaks 350, 335

3-O-n-octadecyl-5,6-O-(1-chloromethylethylidene)-L-ascorbic acid
Analysis calculated: C, 64.5; H, 9.4; O, 19.1; Cl, 7.1; Found: C, 64.5; H, 9.5; O, 19.0; Cl, 7.3.
Titration: pka—9.0
Mass spectrum: peaks at 502, 453
Infrared spectrum: $\nu$ at 1705, 1775, 2860, 2940, 3040 cm$^{-1}$ 3-O-n-pentadecyl-5,6-O-(1-methylethylidene)-L-ascorbic acid
Infrared spectrum: $\nu$ at 1710, 1780, 2870, 2940 cm$^{-1}$
Titration: pKa—10.9
Mass spectrum: peaks at 426, 411.

2,3-O-bis(n-pentadecyl)-5,6-O-(1-methylethylidene)-L-ascorbic acid
No titratable groups.
Infrared spectrum: $\nu$ at 1690, 1770, 2885, 2940, cm$^{-1}$.
Mass spectrum: peaks at 636, 621.

3-O-(3-fluorobenzyl)-5,6-O-(1-methylethylidene)-L-ascorbic acid
Analysis calculated: C, 59.3; H, 5.3; F, 5.9; Found: C, 59.1; H, 5.1; F, 5.6.
Infrared spectrum: $\nu$ at ;b 1705, 1760, 3320 cm$^-$
Mass spectrum: peaks at 324, 309

2,3-bis(O-4-cyanobenzyl)-5,6-O-(1-methylethylidene)-L-ascorbic acid
Mass spectrum: peaks at 446, 431
No titratable groups.
Infrared spectrum: $\nu$ at 1690, 1780, 2250, 2910, 3000 cm$^{-1}$ 2,3-bis(O-2-methylbenzyl)-5,6-O-(1-methylethylidene-L-ascorbic acid
Infrared spectrum: $\nu$ at 1705, 1780, 2950, 3020 cm$^{-1}$
No titratable group.
Mass spectrum: peaks at 424, 409.

3-O-(11-hydroxyundecyl)-5,6-O-(1-methylethylidene)-L-ascorbic acid
Infrared spectrum: $\nu$ at 1710, 1780, 2950, 3540 cm$^{-1}$
Titration: pKa=10.79
Mass spectrum: M+ 387

3-O-(4-cyanobutyl)-5,6-O-(1-methylethylidene)-L-ascorbic acid
Titration: pKa=10.40
Infrared spectrum: $\nu$ at 1700, 1765, 3000, 3515 cm$^{-1}$
Mass spectrum: peaks at 297, 282

EXAMPLE 7

Preparation of 2-O-Benzyl-3-O-n-hexadecyl-L-ascorbic acid.

A solution of 0.933 g. of 3-O-n-hexadecyl-L-ascorbic acid in 7.5 ml. of anhydrous DMF was added slowly at ambient temperature under a nitrogen atmosphere to a suspension of 2.45 millimoles of NaH in 10 ml. of anhydrous DMF in a 50 ml., 3-neck round-bottom flask equipped with magnetic stirrer, drying tube and dropping funnel. The reaction mixture was stirred for 25 minutes (until H$_2$ evolution stopped) at which time the sodium salt (on the 2-hydroxy) of 3-O-n-hexadecyl-L-ascorbic acid had formed. A solution of 0.295 g. of benzyl chloride in 2 ml. of anhydrous DMF was added. The reaction mixture was stirred at ambient temperature for about 50 minutes. The reaction temperature was then raised to 90° C., at which temperature stirring was continued for an additional 50 minutes. The reaction mixture was cooled and saturated aqueous sodium chloride (brine) added. The resulting aqueous mixture was extracted with ethyl acetate. The ethyl acetate extract was washed with brine and dried. The dried extract was decolorized with charcoal, filtered and the volatile constituents removed in vacuo. The resulting yellow syrup was chromatographed over silica gel 60 using 1:9 ethyl acetate-toluene as the eluant. Fractions shown by TLC to contain the desired product were combined and the solvent removed therefrom. 694 mg. (62% yield) of a yellow waxy solid comprising purified 2-O-benzyl-3-O-n-hexadecyl-L-ascorbic acid were obtained.

Analysis calculated: C, 70.99; H, 9.45; Found: C, 71.05; H, 9.63.

Proton magnetic resonance spectrum: $\nu$ 7.35 (singlet-5H), 5.1 (singlet-2H).

Mass spectrum: peaks at 490 (M+), 459, 398, 338, 295, 177, 116, 91.

Infrared spectrum: $\nu$ at 1761, 1672 cm$^{-1}$

As previously stated, the compounds of this invention inhibit the action of angiogenesis factor in promoting the development of blood vessels (as part of the growth process) by tumors, by which mechanism the tumor is able to form an adequate blood supply system. One method of demonstrating such angiogenesis factor inhibitory action in vivo is by the following test procedure.

Lysosomal-mitochondrial pellets containing angiogenesis factor are prepared from 3683 Morris hepatoma. The pellet is diluted with 7-8 ml. of 15% ficoll. With this dilution, 8-10 serpentine vessels will be produced per 0.2 cc. injection as described below for the control group. The dilution may be adjusted upward or downward to bring the number of serpentine vessels induced within the 8-10 range so as to provide comparable concentrations of angiogenesis factor per lysosomal-mitochondrial preparation.

Next, 15 SPF/ND4 female mice weighing 20-22 g. are shaved on the left side and then divided into three groups of five each. One group (drug group) is injected subcutaneously and laterally with 0.20 cc. of the lysosomal-mitochondrial preparation diluted with 15% ficoll. This group of mice is then dosed individually by the intraperitoneal route with 0.5 cc. of a solution or suspension in a standard vehicle containing the compound under test, usually at an initial dose level of 300 mg./kg. If this dose level is toxic, two-fold dilutions are made until all mice survive a single dose. The second group of mice (control group) is injected subcutaneously and laterally with 0.2 cc. of the lysosomal-mitochondrial suspension diluted with 15% ficoll and dosed intraperitoneally with 0.5 cc. of the vehicle alone. The third group (negative control) is injected with ficoll solution only (no treatment with drug or vehicle). The mice are sacrificed after 24 hours. Each mouse is placed on its side on a dissecting board with the shaved side up. Starting at the flank, the skin is cut straight to the back of the animal. A similar cut is made behind the front leg. Then the skin is cut along the back making a flap of about one inch by two inches. The skin is carefully separated from the connective tissue using forceps and a scalpel. The skin flap is then laid back exposing the lysosomal-mitochondrial implant which is attached to the skin. The skin flap is gently flattened out and with the use of a binocular dissecting scope, serpentine vessels are observed around the lysosomal-mitochondrial implant and their number counted. All observations of the number of serpentine vessels are made at the same power of the microscope (1X). The average number of serpentine vessels for each group is calculated. The percent inhibition is then calculated according to the following equation.

$$\% \text{ inhibition} = \left(1 - \frac{\overline{sv} \text{ (drug group)}}{\overline{sv} \text{ (control group)}}\right) \times 100$$

where $\overline{sv}$ = average number of serpentine vessels.

If the negative control group described above has any serpentine vessels, the test is invalid due to contamination of the ficoll solution.

Tables I, II and III which follow give the results of these tests.

Table I covers compounds according to formula I above in which R$^2$ and R$^3$ are both H, table II covers compounds in which R$^2$ and R$^3$ form a 1-methylethylidene group, and Table III compounds in which R$^2$ plus R$^3$ equal a benzylidene group or other group.

One of the compounds of this invention, 3-O-n-octadecyl-5,6-O-(1-methylethylidene)-L-ascorbic acid was tested at a series of dose levels for its ability to inhibit tumor angiogenesis and the results of these tests are set forth in Table IV.

TABLE 1

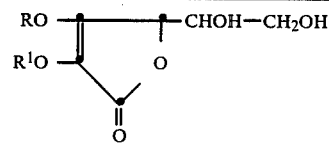

| R | R$^1$ | average % inhibition | range Dose in mg./kg. |
|---|---|---|---|
| 2,6 dichlorobenzyl | H | 56 | 150-300 |
| n-octadecyl | H | 82 | 25-300 |
| Br(C$_2$H$_4$)OCH$_2$CH$_2$ | H | 36 | 300 |
| phthalimido-C$_2$H$_4$ | H | 55 | 300 |
| 3-phenoxypropyl | H | 68 | 300 |
| 3-bromobenzyl | H | 74 | 300 |
| 3-fluorobenzyl | H | 52 | 25 |
| 10-carboxy n-decyl | H | 41 | 25 |
| n-pentadecyl | H | 50 | 300 |
| n-pentadecyl | n-pentadecyl | 38 | 25-300 |
| n-dodecyl | H | 59 | 25-300 |
| 3-methylbenzyl | H | 54 | 25 |
| 3-trifluoromethyl-benzyl | H | 53 | 25-300 |
| 3-chlorobenzyl | H | 41 | 25 |
| 2,5-dimethylbenzyl | H | 47 | 25-300 |
| n-octadecyl | n-octadecyl | 52 | 25 |
| 4-chlorobenzyl | H | 36 | 25-300 |
| n-hexadecyl | H | 31 | 25 |
| n-hexadecyl | n-hexadecyl | 13 | 25-150 |
| 2-chlorobenzyl | H | 55 | 25 |

TABLE 2

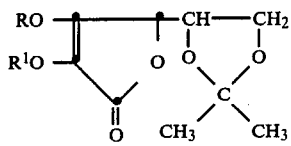

| R | R¹ | % inhibition | Range Dose in mg./kg. |
|---|---|---|---|
| H | H | 48 | 10 |
| methyl | H | 15 | 10 |
| n-butyl | H | 60 | 10 |
| n-hexyl | H | 41 | 10 |
| n-decyl | H | 48 | 10 |
| n-octadecyl | H | 38–82 | 25–300 |
| CH—O—$C_2H_4$ | H | 28–61 | 10–240 |
| Br($C_2H_4$)—O—$C_2H_4$ | H | 71 | 240 |
| $C_2H_5OCOCH_2$ | H | 12 | 10 |
| 4-nitrobenzyl | H | 42–85 | 150 |
| 3-phenoxypropyl | H | 36 | 150 |
| phthalimidoethyl | H | 30 | 120 |
| 3-fluorobenzyl | H | 27–82 | 25 |
| 11-hydroxy-n-undecyl | H | 67 | 150 |
| 4-cyano-n-butyl | H | 37–72 | 37.5–150 |
| n-pentadecyl | n-pentadecyl | 15–85 | 25–150 |
| n-octadecyl | n-octadecyl | 18–85 | 25 |
| 4-cyano-n-butyl | 4-cyano-n-butyl | 47–82 | 25–150 |
| 4-cyanobenzyl | 4-cyanobenzyl | 36–91 | 25 |
| 4-fluorobenzyl | 4-fluorobenzyl | 45 | 37.5 |
| n-pentadecyl | H | 15–85 | 25–150 |

TABLE 3

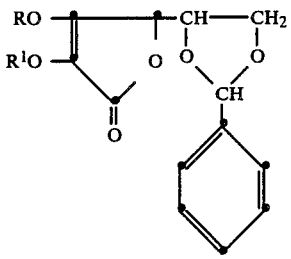

| R | R¹ | % inhibition* |
|---|---|---|
| n-butyl | H | 60 |
| 2-methoxyethyl | H | 31 |

*150 mg./kg. dose intraperitoneally

| Evaluation of 3-O—n-octadecyl-5,6-O—(1-methylethylidene)-L-ascorbic acid | |
|---|---|
| Intraperitoneal Dose in mg./kg. | % inhibition |
| 240 | 71, 78 = $\overline{74.5}$ |
| 120 | 66, 78, 75, 71 = $\overline{72.5}$ |
| 60 | 72, 50 = $\overline{62.5}$ |
| 30 | 58, 38 = $\overline{48}$ |
| 15 | 45, 17 = $\overline{32}$ |

In addition, the compounds of this invention have found utility as angiogenesis inhibitors in metastatis formation. Such activity has been found in an artificial metastasis model using Madison lung (M 109) carcinoma which metastasizes preferentially to lungs and is not overly sensitive to chemotherapeutic agents. The test is carried out as follows.

MADISON LUNG METASTASIS ASSAY

The Madison (M109) lung carcinoma is carried as a transplantable line in syngeneic BALB/C mice. This tumor line was obtained from the tumor bank at Mason Research Institute, Worcester, Mass. For tumor metastasis studies, a subcutaneously-grown tumor is aseptically excised, minced into small pieces with a scissors, and gently trypsinized at room temperature to obtain a single cell suspension. The cells are suspended in RPMI-1640 medium (M. A. Bioproducts, Walkersville, MD). Viable M109 cells are determined by trypan blue exclusion, and the cell concentration is determined with a hemocytometer. The cells are adjusted to $1 \times 10^5$ viable cells/ml. of medium. M109 cells are injected i.v. into normal, male BALB/C mice. Inoculum volume per mouse is 0.2 ml. ($2 \times 10^4$ cells). Drugs are administered i.p. to randomized groups of 10 mice 2 days prior to tumor cell inoculation. Controls receive mock injections of 0.5 ml. buffer. Daily mortality is monitored, and median survival times are determined for each group. The results of this test on 3-O-n-octadecyl-L-ascorbic acid are recorded in Table 5. Cytoxan was employed as a positive control. In the Table, column 1 gives drug treatment and columns 2 and 3 measures number of lesions±standard error per lung on days 30 and 42.

| Drug Treatment | Mean No. of Lesions ± S.E./Lung | |
|---|---|---|
| | Day 30 | Day 42 |
| Emulphor control | 15.8 ± 4.6 | 20.6 ± 1.8 |
| Cytoxan (30 mg./kg.)* | 8.4 ± 1.5 | — |
| 3-O—n-octadecyl-L-ascorbic acid (35 mg./gk.) | 1.8 ± 1.2 | 18.6 ± 1.3 |
| 3-O—n-octadecyl-L-ascorbic acid + Cytoxan (35 + 30 mg./kg.) | 1.6 ± 0.6 | Toxic |

*Cytoxan given every 4th day I.P. starting on day 12.

The growth rate and number of lung metastases in the above experiment were less than usual. A new transplant line was employed in a second determination with lung lesions developing earlier. Table 6 records the results of this experiment; here ascorbic acid was employed as the control drug.

TABLE 6

| Drug Treatment** | Mean No. of Lesions ± S.E./Lung 16 day |
|---|---|
| Emulphor control | 69.8 ± 10.4 |
| ascorbic acid (100 mg./kg.) | 33.8 ± 9.6 |
| 3-O—n-octadecyl-L-ascorbic acid (30 mg./kg.) | 10.7 ± 3.4 |
| 3-O—n-octadecyl-L-ascorbic acid (100 mg./kg.) | 13.0 ± 5.1 |

**All drugs given daily from day 0.

The compounds useful in this invention are relatively non-toxic, having $LD_{50}$'s above 400 or 1000 mg./kg. in mice.

Another laboratory test involving angiogenesis or neovascularization is based on the time period required for a differentiated tumor to become undifferentiated (vascularized). An inflammatory response enhances tumor growth and reduces the lag phase. In this test, rats are injected with a test drug (30 minutes prior to dosing) with ICFA (incomplete Freund's adjuvant) plus India ink intradermally in a shaved area on a rat's back, thus providing a marked injection site. After 3 days of twice daily administration of the test drug followed 30 minutes later by administration of ICFA, the tumor is transplanted on the periphery of the marked injection site. The animals are weighed and the tumor size determined (length+width/2) at weekly intervals for 4 weeks. Morris hepatoma (5123D) was used as the undifferentiated tumor.

Following the above experimental procedure, 10-100 mg. of 3-O-n-octadecyl-L-ascorbic acid administered once or twice a day orally either inhibited the growth of the undifferentiated tumor or delayed its induction from 4-7 days. 0.5 cc. of ICFA were also given once or twice daily subcutaneously to each test rat.

A third laboratory test has been employed to demonstrate the activity of compounds according to I above as inhibitors of angiogenesis. This test method is a collagen arthritis assay carried out as follows.

Type II collagen is isolated from bovine articular cartilage by the method of Strawich and Nimni [Biochemistry, 10, 3905, (1971)]. The collagen is dissolved in 0.1M acetic acid and stored at −20°. Type II collagen solution is diluted to 2 mg./ml. concentration and emulsified thoroughly with an equal volume of incomplete Freund's adjuvant (ICFA). The emulsion containing approximately 0.5 mg. of collagen is injected intradermally to groups of 6 inbred Lewis male rats (Charles River Breeders; 170-200 g.) at various sites in the dorsal area. The hindpaw volumes of each rat is measured and recorded three times a week throughout the test period to assess the inflammatory reaction. The animals receive compounds under test as suspensions in carboxymethylcellulose vehicle, by oral gavage, 5 days per week (Mon.-Fri.). At the end of the test (day 28 or 30), the blood of these animals is drawn by cardiac puncture and the serum anti-type II collagen antibody levels are estimated by passive hemagglutination technique, using glutaraldehyde treated sheep red cells, to which type II collagen is conjugated [Avrameas et al., Immunochemistry, 6, 67, (1969); Andriopoulos et al., Arth. Rheum., 19, 613, (1976)]. The cellular response or delayed-type hypersensitivity response to type II collagen is measured by the radiometric ear index assay (Kostiala, Immunology, 33, 561, 1977). In certain experiments, the bone damage occurring because of immunization with type II collagen and the effects of drugs are determined from the radiographs of the hindpaws of two or three representative animals from each group. Injections of ICFAs alone were employed to some rats as a negative control.

In one experiment carried out according to the above protocol, 3-O-n-octadecyl-5,6-O-(1-methylethylidine)-L-ascorbic acid and 3-O-n-octadecyl-L-ascorbic acid were the test drugs and were administered orally at a 50 mg./kg. dose. The former compound inhibited the swelling of the paw caused by injection of Type II collagen by about 50% and with the latter, paw volumes were not substantially different from those of the ICFA-treated rats (negative controls). In other runs, with 3-O-n-octadecyl-L-ascorbic acid, at the 50 mg./kg. dose leve, paw volumes were 90-100% lower than those of rats immunized with type II collagen but not treated with drugs (positive controls). With 3-O-n-octadecyl-5,6O-(1-methylethylidene)-L-ascorbic acid at the same dose level, the paw volumes were indistinguishable from negative control levels.

At lower dosages with 3-O-octadecyl-L-ascorbic acid, a 12.5 mg./kg. dose decreased paw volumes by about 25%, but at a 17.5 mg./kg. dose, the paw volumes were indistinguishable from controls.

2,3-O-bis(n-octadecyl)-L-ascorbic acid at 12.5 and 25 mg./kg. dose levels also gave decreased paw volumes (33-67%). With 3-O-(m-trifluoromethylbenzyl)-L-ascorbic acid at a 25 mg./kg. dose, paw volumes were substantially the same as ICFA controls.

The following additional drugs gave substantial decreases in paw swelling caused by collagen Type II injection at a drug dose of 15 mg./kg. per os: 3-O-n-heptadecyl-L-ascorbic acid, 2,3O-bis(4-cyanobenzyl)-5,6-(1-methylethylidene)-L-ascorbic acid, 3-O-(4-cyanobutyl)-5,6-(1-methylethylidene)-L-ascorbic acid, and 5,6-O-(1-n-decylethylidene)-L-ascorbic acid.

In utilizing the compounds of this invention an angiogenesis inhibiting agents, either the parenteral or oral route of administration may be employed. For oral dosage, which is preferred, a suitable quantity of a drug according to formula I is mixed with one or more conventional, pharmaceutically acceptable excipients such as starch and the mixture placed in telescoping gelatin capsules, each capsule containing a divided or undivided dose. Alternatively, a mixture of the drug plus starch plus a lubricant plus other pharmaceutically acceptable excipients as required is compressed into tablets each containing from 100 to 500 mg. of active ingredient. The tablets may be scored if lower or divided dosages are to be used. For parenteral administration, the drug is administered in solution or suspension. Each unit dose of the drug for either route of administration will contain an amount of a drug according to I above effective to inhibit angiogenesis. Daily dose levels in mammals would be in the range 10-100 mg./kg. of mammalian body weight.

We claim:

1. The method of inhibiting angiogenesis in collagen-induced arthritis which comprises administering to a mammal in need of treatment an angiogenesis inhibiting dose of a compound of the formula

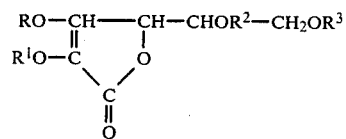

wherein R and $R^1$ are individually H or $CH_2R^4$, except that at least one of R and $R_1$ must be other than H, wherein $R^4$ is $(C_1-C_{21})$alkyl-$R^5$, $(C_2-C_{12})$alkenyl, $(C_2-C_{12})$alkynyl, $(C_3-C_8)$cycloalkyl, $(C_3-C_8)$cycloalkenyl, $(C_7-C_{12})$bicycloalkyl or $(CH_2)_m$ Z, wherein $R^5$ is CN, OH, H, O—$(C_1-C_5)$alkyl, O—$(C_2-C_4)$haloalkyl, phthalimido, $COOR^8$, OZ or $N(CH_3)_2$; m is 0, 1 or 2 and Z is

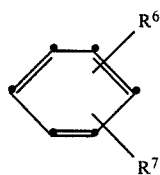

wherein $R^6$ and $R^7$ are individually halo, $CF_3$, H, $(C_1-C_3)$alkyl, O-$(C_1-C_3)$alkyl or $NO_2$ and $R^8$ is H or $(C_1-C_3)$alkyl, except that when $R^4$ is $(C_1-C_{21})$alkyl-$R^5$ and $R^5$ is $O-(C_1-C_5)$alkyl, $O-(C_2-C_4)$haloalkyl or $OZ$, the total number of carbon atoms in $R^4$ is less than 22;

$R^2$ and $R^3$, when taken singly are H, $(C_1-C_{12})$alkyl or $CH_2$-phenyl;

$R^2$ and $R^3$, when taken together, are

wherein $R^9$ is $(C_1-C_{10})$alkyl, halo-substituted $(C_1-C_{10})$alkyl, Z, or $(C_1-C_{10})$alkyl-Z and $R^{10}$ is $R^9$ or H.

2. A method according to claim 1 in which L-ascorbic acid is represented.

3. A method according to claim 1 in which $R^1$ is H and R is $CH_2R^4$, $R^4$ is $(C_1-C_{21})$alkyl-$R^5$, and $R^5$ is H.

4. A method according to claim 2 in which R is $CH_2R^4$, $R^4$ is $(C_1-C_{21})$alkyl-$R^5$ and $R^5$ is CH, OH, H, $O-(C_1-C_5)$alkyl, $O-(C_2-C_4)$haloalkyl or $COOR^8$ wherein $R^8$ is H or $(C_1-C_3)$alkyl.

5. A method according to claim 1 in which R is $CH_2R^4$, $R^4$ is $(CH_2)_mZ$, m is 0, 1 or 2 and Z is naphthyl or phenyl permissibly substituted with one or two, same or different, members of the group halo, $(C_1-C_5)$alkoxy, $(C_1-C_5)$alkyl, nitro, CN, hydroxy, or $CF_3$, and $R^1$ is H or R.

6. A method according to claim 3 in which R is $CH_2R^4$, and $R^1$ is H or $CH_2R^4$, wherein $R^4$ is, same or different, $C_{13}-C_{21}$ straight chain alkyl.

7. A method according to claim 1 in which $R^2$ and $R^3$ taken together represent

wherein $R^9$ and $R^{10}$ are individually, same or different, $(C_1-C_{10})$alkyl.

8. A method according to claim 7 in which $R^9$ and $R^{10}$ are both methyl.

9. A method according to claim 7 in which $R^{10}$ is H and $R^9$ is phenyl or substituted phenyl wherein said substituents are $(C_1-C_5)$alkyl, $CF_3$, halo, nitro, $(C_1-C_5)$alkoxy, OH or cyano.

10. A method according to claim 1 in which both R and $R^1$ are $CH_2R^4$ and $R^4$ is $(C_1-C_{21})$alkyl.

11. A method according to claim 1 in which R is $CH_2R^4$, $R^1$ is H or $CH_2R^4$, $R^4$ is $(C_{13}-C_{21})$alkyl, and $R^2$ and $R^3$ taken together form

in which $R^9$ and $R^{10}$ are individually $(C_1-C_5)$alkyl.

12. A method according to claim 1 in which an ether, ketal or acetal derivative of L-ascorbic acid is administered as the angiogenesis inhibiting drug.

13. A method according to claim 6 in which 3-O-n-octadecyl-L-ascorbic acid is administered.

14. A method according to claim 6 in which 3-O-n-octadecyl-5,6-O-(1-chloromethylethylidene)-L-ascorbic acid is administered.

15. A method according to claim 6 in which 3-O-n-pentadecyl-L-ascorbic acid is administered.

16. A method according to claim 6 in which 3-O-n-heptadecyl-L-ascorbic acid is administered.

17. A method according to claim 5 in which 3-O-m-trifluoromethylbenzyl-L-ascorbic acid is administered.

18. A method according to claim 5 in which 3-O-m-fluorobenzyl-L-ascorbic acid is administered.

19. A method according to claim 5 in which 3-O-m-chlorobenzyl-L-ascorbic acid is administered.

20. A method according to claim 1 in which the drug is administered by the oral route.

* * * * *